US00PP15612P2

(12) United States Plant Patent
Kordes

(10) Patent No.: US PP15,612 P2
(45) Date of Patent: Mar. 1, 2005

(54) MINIATURE ROSE PLANT NAMED 'KORAMGAT'

(50) Latin Name: *Rosa hybrida*
Varietal Denomination: KORamgat

(75) Inventor: Tim-Hermann Kordes, Offenseth-Sparrieshoop (DE)

(73) Assignee: W. Kordes Söhne Rosenschulen GmbH & Co. KG, Offenseth-Sparrieshoop ( * ) Notice: Subject to any disclaimer, the term of this patent is extended or adjusted under 35 U.S.C. 154(b) by 0 days.

(21) Appl. No.: 10/737,607

(22) Filed: Dec. 15, 2003

(51) Int. Cl.[7] ..... A01H 5/00
(52) U.S. Cl. ..... Plt./118
(58) Field of Search ..... Plt./118, 119

(56) References Cited

PUBLICATIONS

Application for PBR in EU, Dec. 16, 2002, W. Kordes' Söhne.
QZ App. # 2002/2091, Dec. 20, 2002, W. Kordes' Söhne.
QZ Grant EU/CPVO 12994, Apr. 5, 2004, W. Kordes' Söhne.

*Primary Examiner*—Bruce R. Campell
*Assistant Examiner*—S B McCormick-Ewoldt

(57) ABSTRACT

A new and distinct variety of miniature rose with long lasting, novel yellow orange flowers and dark green and attractive foliage. It exhibits compact, uniform growth and flowering under greenhouse conditions, when grown as a potted floral plant. The new variety propagates well from cuttings and by grafting. This new and distinct variety has shown to be uniform and stable in the resulting generations from asexual propagation.

1 Drawing Sheet

Genus, species and variety denomination: The botanical classification of the new rose plant is *Rosa hybrida*, variety denomination 'KORamgat'.

BACKGROUND OF THE INVENTION

The new variety of miniature rose plant of the present invention originated from a controlled crossing in a breeding program between 'KORbritta', described and illustrated in U.S. Plant Pat. No. 11,146 issued on Dec. 7, 1999; and 'KORrogilo' (not patented), a variety by the same breeder.

The two parents were crossed and the resulting seeds were planted in a controlled greenhouse environment. The resulting seedlings exhibited distinctive physical and biological characteristics. The new rose plant was selected in June, 2000 as a single plant from the seedling beds due to its superior characteristics and asexually propagated for further evaluation. This new and distinctive miniature rose variety is named 'KORamgat'.

SUMMARY OF THE INVENTION

The new rose plant may be distinguished from its seed parent, 'KORbritta', by the following combination of characteristics:

1. The base of the petal of 'KORbritta' has a small area with a slightly greenish cast at the point of attachment, while 'KORamgat' does not; and
2. The flowers of 'KORbritta' are more amber in color.

The new rose plant may be distinguished from its pollen parent, 'KORrogilo' by the following combination of characteristics:

1. The pollen parent has larger flowers;
2. The flowers of the pollen parent are a more intense yellow color; and 3. The plant height of the pollen parent in the nursery is approximately 100 cm, while the height of 'KORamgat' is less than 40 cm.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers on upright stems;
3. Resistance to diseases encountered in greenhouse and nursery culture; and
4. Suitability for production from softwood cuttings in floral and nursery containers;

This combination of traits is not present in prior rose cultivars. These objectives have been substantially achieved and distinguish 'KORamgat' from all other varieties of which we are aware.

As part of the rose development program, Tim-Hormann Kordes germinated the seeds from the aforementioned hybridization and conducted evaluations and observations on the resulting seedlings in a controlled environment at W. Kordes' Söhne Nursery in Sparrieshoop, Germany. Asexual reproduction of 'KORamgat' by softwood cuttings was first done Jul. 1, 2000 at the Rosa-Danica Nursery in Odense, Denmark.

This initial and other subsequent propagations conducted in controlled environments show that the foregoing and all other characteristics of 'KORamgat' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORamgat'. Specifically illustrated in SHEET ONE.

DETAILED DESCRIPTION

Figures 1, 2, 3, 4, 5, 6, 7, 8, 9, 10:
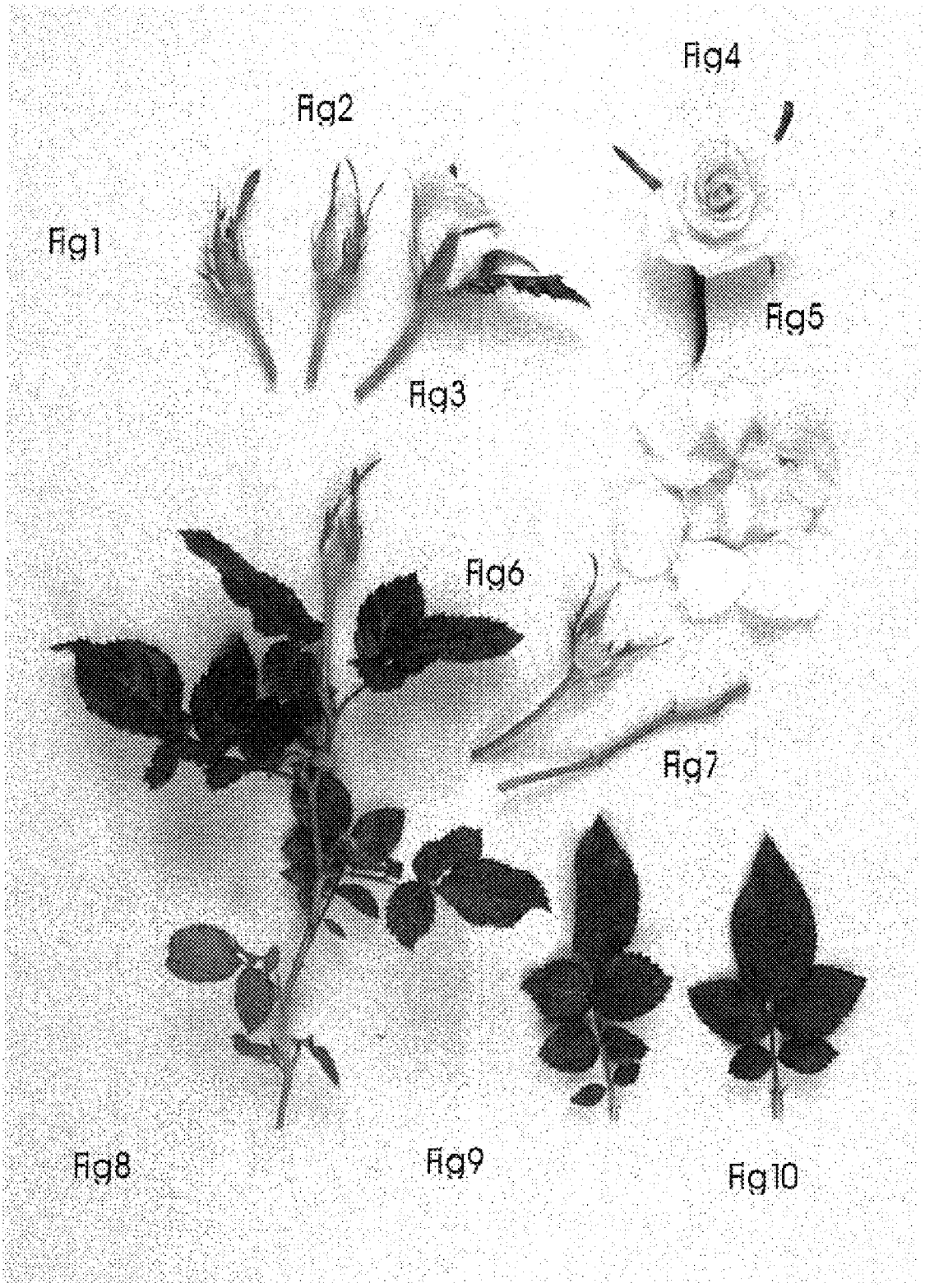
FIG. 1. Tight flower bud.
FIG. 2. Partially opened bud.
FIG. 3. Half open bloom.
FIG. 4. Open bloom.
FIG. 5. Flower petals, detached.
FIG. 6. Sepals, dissected receptacle, and peduncle.
FIG. 7. Stem exhibiting thorns.
FIG. 8. Stem showing branching and the attachment of leaves, a bud, and a peduncle.
FIG. 9. A single leave.
FIG. 10. A single leave.

The following is a description of 'KORamgat', as observed in its growth in glasshouses in Odense Denmark on plants of 12 weeks of age and on outdoor budded nursery plants in Sparrieshoop, Germany of 1 year of age. Color references are made using The Royal Horticultural Society (London, England) Colour Chart, 2001 except where common terms of color are used.

For a comparison, several physical characteristics of the rose variety 'KORbritta', a rose variety from the same inventor described and illustrated in U.S. Plant Pat. No. 11,146 and issued on Dec. 7, 1999 are compared to 'KORamgat' in Chart 1:

CHART 1

| Character | 'KORamgat' | 'KORbritta' |
|---|---|---|
| Color, inner side of innermost petals: | Yellow Group 13B. | Yellow-Orange Group 21B. |
| Color, outer side of petals: | Yellow Group 6C-13B. | Yellow-Orange Group 21B. |
| Petal base, at point of attachment: | No distinctive coloration. | Small green area with greenish cast. |

Parents:

*Seed parent.*—'KORbritta'.

*Pollen parent.*—'KORrogilo'.

Classification:

*Botanical classification.*—*Rosa hybrida.*

*Commercial classification.*—Miniature.

FLOWER AND FLOWER BUD

Blooming habit: Recurrent.

*Flower bud.*—Size: Upon opening, 28–32 mm in length from base of receptacle to end of bud. Bud form: High centered to pointed ovoid. Bud color: As sepals first unfold, bud color is Yellow Orange Group 20B. When ¼ open, the upper surface of petals is a blend of Yellow-Orange Group 20C and Yellow-Orange Group 22D; and the lower surface color transitions from Yellow Group 6C towards the base to Yellow Group 6A on the margin. Sepals: Size: 30–50 mm long and 6–8 mm wide. The longer sepals have the most pronounced foliaceous appendages. Margins: Weak foliaceous appendages on three of the five sepals. Quantity: Five. Surface texture: Slightly pubescent. Stipitate glands are present on the margins. Color: Upper surface Green Group 138A. Lower surface Green Group 137A.

*Receptacle.*—Surface: With moderate amounts of short white hairs. Color: Yellow-Green Group 146B. Shape: Funnel. Size: 4–5 mm (h) 7–8 mm (w).

*Peduncle.*—Surface: With fine hairs and a limited number of stipitate glands. Length: 35–40 mm average length. Diameter: 1.8–2.2 mm. Color: Yellow-Green Group 146B. Strength: Upright and strong.

*Borne.*—Singly.

*Anthocyanin.*—Little to none on stems or petioles.

Flower bloom:

*Fragrance.*—Light.

*Duration.*—The blooms have a duration on the plant of approximately 15 to 18 days. As a cut flower, the blooms last 10 to 12 days.

*Size.*—Medium to medium-large for a 8–11 cm pot rose plant. Average flower diameter is 45–50 mm when open.

*Form.*—Shape of flower when viewed from the side: Upon opening, upper part: Flattened convex to convex. Upon opening, lower part: Convex. Open flower, upper part: Flattened convex. Open flower, lower part: Flattened convex to convex.

Color:

*Upon opening, petals.*—Margins of outermost and innermost petals with intonations of Orange Group 28C. No distinctive coloration at petal base observed. Outermost petals: Outer Side: Yellow Group 6C. Inner Side: Yellow Group 6B. Innermost petals: Outer Side: Yellow Group 13B. Inner Side: Yellow Group 13B.

*After opening, petals.*—No distinctive coloration at petal base observed. Outermost petals: Outer Side: A blend of Yellow Group 6C and Yellow Group 6D. Inner Side: A blend of Yellow Group 6B and Yellow Group 6C. Innermost petals: Outer Side: A blend of Yellow Group 13B and Yellow Group 13C. Inner Side: Yellow Group 13B. Variegations: None.

General tonality: A blend of colors. On an open flower the center of the flower is Yellow-Orange Group 22B–22A. The outer rows of petals exhibit a tonality of Yellow Group 8C. No change in the general tonality at the end of 3 to 4 days. Afterwards, general tonality is a blend of Yellow Group 8C and Yellow Group 13C with intonations of Orange Group 28D.

Petals:

*Petal count.*—Approximately 20 to 24 petals under normal conditions.

*Petal reflex.*—Outermost petals reflex somewhat.

*Petal edge.*—Entire.

*Petal shape.*—Orbicular to broadly obovate. Apex shape is round. Shape of base is acute to rounded.

*Petal size.*—10–22 mm long; 8–52 mm wide, with the inner petals being smaller.

*Thickness.*—Above average.

*Texture.*—Smooth.

*Petal arrangement.*—Generally in a regular pattern with overlapping edges. Petals unfurl as bloom opens.

*Petaloids.*—Present. Quantity: 2–3 generally present. Size: 8.0–12.0 mm long; 4.0–6.0 mm wide. Texture: Smooth. Shape: Linear to narrowly oblanceolate, with variable apex and narrow base. Color: Inner and outer side Yellow Group 13B with intonations of Orange Group 28C.

Reproductive organs:

*Pistils.*—Quantity: Approximately 40–45 pistils per flower. Stigmas: Location: Positioned at the same level as outer one-half of the anthers, and slightly superior to the innermost one-half. Color: Green-White Group 157A. Styles: Length: 8–10 mm long. Color: Green-White Group 157A. Below the stigma, a band approximately 1–2 mm in height with strong intonations of Red-Purple Group 58A. Below this band, Green-White Group 157A.

*Stamens.*—Approximately 40–45 on average and regularly arranged around the styles. Anthers: Size: 1.5–2.0 mm long. Color: Yellow-Orange Group 22A–22B. Pollen: Generally present. Average abundance. Color: Yellow-Orange Group 22A–22B. Filaments: Color: Yellow-Green Group 150C. Length: 6–8 mm.

THE PLANT

*Plant growth.*—Vigorous. Upright to bushy. When grown as a 8 to 11 cm pot plant, the average height of the plant itself is 18–20 cm and the average width is 16–18 cm. When grown as a budded nursery plant the average plant height is 40 cm and the average plant width is 30 cm.

*Stems.*—Stem color: Young wood: Green Group 138A. Older wood: Green Group 138A. Stem surface: Young wood: Smooth. Older wood: Smooth.

Prickles: Present. Most prickles small and thin. Incidence: Average. 4–6 per 10 cm of stem. Size: Average length: 2 mm–3 mm. Some to 5 mm. Color: Green-White Group 157A with intonations of Greyed-Red Group 181A. Shape: Linear.

*Leaves and leaflets.*—Normal leaves in middle of the stem with 5 leaflets. A few stems exhibit leaves with 7 leaflets. Leaf size: 70–80 mm (l)×45–55 mm (w). Quantity: Average to above average. Glossiness on upper side: Moderately glossy. Color, mature foliage: Upper Leaf Surface: Green Group 137A. Lower Leaf Surface: Green Group 146B. Color, juvenile foliage: Upper Leaf Surface: Green Group 138A. Lower Leaf Surface: Green Group 146B. Anthocyanin intonation: Greyed-Red Group 181A intonations present on leaf margins of developing leaves.

*Stipules.*—Size: 10 mm to 12 mm in length. Stipule color: Green Group 138A. Presence of stipitate glands: Limited numbers on margins.

*Petiole.*—Length: 10 mm to 20 mm. Diameter: 1.4–1.6 mm. Petiole color: Green Group 138A. Margins: Anthocyanin: Absent. Limited numbers of stipitate glands and small fine white hairs on margins and underneath. Prickles: Several small prickles underneath. Color: Greyed-Red Group 179D.

*Petiole rachis.*—Rachis color: Green Group 138A. With a few small prickles underneath. Margins: With limited numbers of stipitate glands and small fine white hairs.

*Leaflets.*—Leaflet: Pointed oval. Average Size of Terminal Leaflet: 42–44 mm long; 24–26 mm wide. Margins: Finely serrated. Texture: Average texture. Nearly smooth.

Hips/seed formation: None observed. The plant has not been grown to the stage of hip and seed development due to its use as a flowering potted plant.

Winter hardiness: Due to the variety's principal use in greenhouses, winter hardiness has not been evaluated.

Disease resistance: Above average resistance to mildew and Botrytis under normal growing conditions in Odense, Denmark.

I claim:

1. A new and distinct variety of miniature rose plant characterized by the following combination of characteristics:

(a) forms, attractive peach-yellow flowers;

(b) exhibits a compact and bushy growth habit;

(c) is suited for greenhouse culture in pots from softwood cuttings; and;

(d) exhibits durable flowers and foliage suitable for distribution in the floral industry;

substantially as herein illustrated and described.

* * * * *